United States Patent [19]

McClure et al.

[11] 4,053,522
[45] Oct. 11, 1977

[54] PREPARATION OF BISPHENOLS

[75] Inventors: James D. McClure, Houston, Tex.; Friedrich E. Neumann, Moraga, Calif.

[73] Assignee: Shell Oil Company, Houston, Tex.

[21] Appl. No.: 688,875

[22] Filed: May 21, 1976

[51] Int. Cl.² .................... C07C 37/20; C07C 39/16
[52] U.S. Cl. .................................................. 260/619 A
[58] Field of Search .................................... 260/619 A

[56] References Cited

U.S. PATENT DOCUMENTS

| | | | |
|---|---|---|---|
| 3,049,568 | 8/1962 | Apel et al. | 260/619 A |
| 3,049,569 | 8/1962 | Apel et al. | 260/619 A |
| 3,153,001 | 10/1964 | Apel et al. | 260/2.2 R |
| 3,172,916 | 3/1965 | Wagner et al. | 260/619 A |
| 3,221,061 | 11/1965 | Grover et al. | 260/619 A |
| 3,242,219 | 3/1966 | Farnham et al. | 260/619 A |
| 3,242,220 | 3/1966 | Apel et al. | 260/619 A |
| 3,282,875 | 11/1966 | Connolly et al. | 260/29.6 |
| 3,394,089 | 7/1968 | McNutt et al. | 260/619 A |
| 3,496,239 | 2/1970 | Hamilton et al. | 260/619 A |
| 3,634,341 | 1/1972 | Gammill et al. | 260/2.2 R |
| 3,760,006 | 9/1973 | Gammill et al. | 260/619 A |
| 3,882,093 | 5/1975 | Cavanaugh et al. | 260/79.3 MU |

*Primary Examiner*—Norman Morganstern
*Attorney, Agent, or Firm*—Dean F. Vance

[57] ABSTRACT

A process and catalyst for the preparation of bisphenols is disclosed. The process involves contacting a phenol with a ketone in the presence of a solid perfluorinated polymer catalyst having pendent sulfonic acid groups which are partially neutralized with a mercaptoamine.

7 Claims, No Drawings

PREPARATION OF BISPHENOLS

BACKGROUND OF THE INVENTION

Bisphenols produced from the condensation of phenols, particularly the bisphenol produced from the condensation of phenol per se and acetone enjoy a growing importance as chemical intermediates, particularly in the fields of epoxy resins and polycarbonate resins.

The most important bisphenol, 2,2-bis(4-hydroxyphenyl)propane (also called para, para-diphenylolpropane or Bisphenol A), is generally prepared by reacting phenol and acetone in the presence of an acidic catalyst such as hydrochloric acid along with a sulfur compound such as methyl mercapton as a co-catalyst. This method is disclosed in U.S. Pat. No. 2,730,552. However, the reaction between phenol and acetone to form 2,2-bis(4-hydroxyphenyl)-propane also forms a number of byproducts including 2-(2-hydroxyphenyl)-2-(4-hydroxyphenyl)propane, also called ortho, para-diphenylolpropane, which is an isomer of 2,2-bis(4-hydroxyphenyl)propane. Further impurities include 2,2-bis(2-hydroxyphenyl)propane, higher condensation products such as trisphenols (condensation products of three moles of phenol and two moles of acetone) and chroman derivatives (internal condensation products of two moles of phenol and two moles of acetone), plus still higher condensation products in the form of resins and tars. In addition, a major drawback to the use of mineral acid catalysts is that any acid present in the product must be neutralized or washed out before the product is recovered. All liquid catalyst systems will have the problem of removing the liquid catalyst from the product stream.

In order to combat some of these above-noted problems, various ion-exchange resins, either alone or in combination with a mobile co-catalyst such as mercapton, have been disclosed to catalyze the condensation reaction of a ketone with a phenol to produce bisphenols. Among the various processes are those disclosed in U.S. Pat. Nos. 3,049,568; 3,049,569; 3,153,001; 3,172,916; 3,221,061; 3,242,219; 3,242,220; 3,394,089; 3,496,239; 3,634,341; and 3,760,006.

A new solid ion exchange resin has been found that gives a much higher conversion at high selectivities than the previously known commercial catalysts.

SUMMARY OF THE INVENTION

The present invention is a process for the production of bisphenols which comprises contacting a phenol and a ketone in the liquid phase at a temperature of between about 20° C and about 150° C with a solid perfluorinated polymer catalyst having pendent sulfonic acid groups modified by the neutralization of between about 5 and about 50 percent of the sulfonic acid groups with a $C_1$-$C_4$ alkyl mercaptoamine wherein said solid perfluorinated polymer catalyst prior to partial neutralization contains a repeating structure selected from the group consisting of:

a)

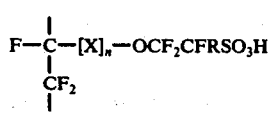

or b)

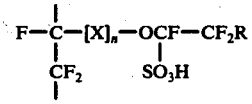

where n is 0, 1 or 2; R is a radical selected from the group consisting of fluorine and perfluoroalkyl radicals having from 1 to 10 carbon atoms; and X is selected from the group consisting of:

$[O(CF_2)_m]$, $[OCF_2CFY]$ or $[OCFYCF_2]$ where m is an integer from 2 to 10 and Y is a radical selected from the class consisting of fluorine and the trifluoromethyl radical.

The present catalyst has been found to be a very active and selective catalyst for the production of 2,2-bis(4-hydroxyphenyl)propane. As compared to an aminoethanethiol-modified Amberlyst 15 acid catalyst, the catalyst of instant invention gives acetone conversions that are 20 to 30 percentage points higher at 4° C lower temperature with a slightly higher selectivity to the desired product.

DETAILED DESCRIPTION OF THE INVENTION

The catalyst employed in the present invention is a solid at reaction conditions. The catalyst prior to partial neutralization broadly comprises a perfluorinated polymer having acid groups in the amount of about 0.01 to 5 mequivalents gram per catalyst.

In a specific embodiment, the polymer catalyst prior to partial neutralization contains a repeating structure selected from the group consisting of:

a)  I

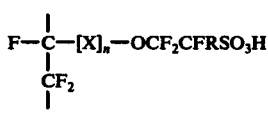

or b)  II

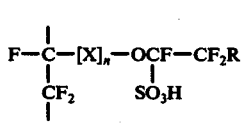

where n is 0, 1 or 2; R is a radical selected from the group consisting of fluorine and perfluoroalkyl radicals having from 1 to 10 carbon atoms; and X is selected from the group consisting of:

$[O(CF_2)_m]$, $[OCF_2CFY]$ or $[OCFYCF_2]$ where m is an integer from 2 to 10 and Y is a radical selected from the class consisting of fluorine and the trifluoromethyl radical. In a preferred embodiment, n is 1 or 2, Y is a trifluoromethyl radical, R is fluorine, and m is 2. Catalysts of the above-noted structure typically have a molecular weight of between about 1,000 and 500,000 daltons.

Polymer catalysts of the above-noted structure I and II can be prepared in various ways. One method, disclosed in Connolly et al, U.S. Pat. No. 3,282,875 and Cavanaugh et al, U.S. Pat. No. 3,882,093, comprises polymerizing vinyl compounds of the formula:

$$CF=CF[X]_nOCF_2CFRSO_3H \qquad III$$

or $$\begin{array}{c} CF=CF[X]_nOCFCF_2R \\ | \\ SO_3H \end{array} \qquad IV$$

in a perfluorocarbon solvent using a perfluorinated free radical initiator. Since the vinyl ethers are liquid at reaction conditions, it is further possible to polymerize and copolymerize the vinyl ethers in bulk without the use of a solvent. Polymerization temperatures vary from −50° to +200° C depending on the initiator used. Pressure is not critical and is generally employed to control the ratio of the gaseous comonomer to the fluorocarbon vinyl ether. Suitable fluorocarbon solvents are known in the art and are generally perfluoroalkanes or perfluorocycloalkanes, such as perfluoroheptane or perfluorodimethylcyclobutane. Similarly, perfluorinated initiators are known in the art and include perfluoroperoxides and nitrogen fluorides. It is also possible to polymerize the vinyl ethers of structure III or IV in an aqueous medium using a peroxide or a redox initiator. The polymerization methods employed correspond to those established in the art for the polymerization of tetrafluoroethylene in aqueous media.

It is also possible to pepare catalysts of structure I and II by copolymerizing the vinyl ethers of structure III or IV with perfluoroethylene and/or perfluoro-alpha-olefins. A preferred copolymer prepared by polymerizing perfluoroethylene with a perfluorovinyl ether containing attached sulfonic acid groups would have the following structure:

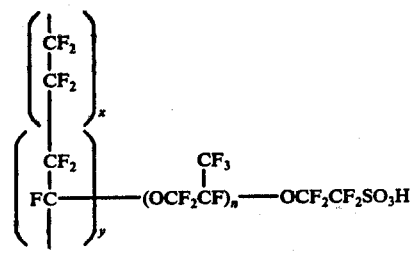

wherein n = 1 or 2 and the ratio of x over y varies from about 2 to about 50. The polymer of structure V is available commercially under the tradename of NAFION ® resin. Catalysts of the above-noted structure V offer the advantages of high concentrations of accessible acid groups in a solid phase.

As shown by comparing the following Illustrative Embodiments, the perfluorinated polymer absent partial neutralization with an alkyl mercaptoamine has a significantly lower conversion and selectivity than does the same catalyst with partial neutralization.

Suitable mercaptoamines for the partial neutralization of the polymer catalyst are $C_1$–$C_4$ alkyl mercaptoamines such as 2-mercaptoethylamine, 2-mercaptoisopropylamine and 3-mercaptobutylamine. While mercaptoamines having primary amino groups are preferred, secondary and tertiary amines are also effective in the partial neutralization. Normally these $C_1$–$C_4$ alkyl mercaptoamines are prepared and isolated as an amine salt, often as the hydrochloride. Since these amine salts undergo a facile exchange reaction with the slurry of water-swollen resin, they can be used directly in the preparation of the present catalyst. However, the free mercaptoamines are, of course, also suitable. Another useful neutralizer is 2,2-dimethylthiaxolidine.

To obtain the improved catalyst of the instant invention, the polymer catalyst of structure I or II is partially neutralized with the $C_1$–$C_4$ alkyl mercaptoamine either by direct neutralization of the polymer catalyst with the mercaptoamine or by exchange with its amine salt. Either reaction is essentially quantitative and can be carried out by adding a calculated amount of the alkyl mercaptoamine to an aqueous slurry of the polymer catalyst in acid form. The degree of neutralization is readily verified by measuring the ion exchange capacity of the polymer catalyst before and after partial neutralization. The theorized partial structure of a 2-mercaptoethylamine neutralized catalyst is:

$$\sim OCF_2CF_2SO_3^-NH_3^+CH_2CH_2SH \qquad VI$$

Preferably, between about 5 and about 50 percent of the acid groups of the polymer catalyst should be neutralized with the mercaptoamine, more preferably between about 20 and about 40 percent of the groups. Very good results are obtained when about 30% of the groups are neutralized.

The phenolic reactant employed must be unsubstituted in the para position, but can be substituted with one or more alkyl, halo or other similiar non-reactive groups in the positions ortho and meta to the phenolic group. Suitable phenols include phenol per se (benzophenol), o- and m-cresol, o- and m-chlorophenol, o-bromophenol, o-sec.-butylphenyl, o-t-butylphenol, 2,6-dibromophenol, 2,6-di-t-butylphenol, 6-chloro-o-cresol, and o-phenylphenol. Much preferred is phenol per se.

As the ketone reactant, methyl ketones such as acetone, methyl ethyl ketone, methyl isobutyl ketone and acetophenone are preferred. However, cyclohexanone and other cyclic ketones as well as halo substituted methyl ketones like 1,2-dichloroacetone can also be used. Much preferred is acetone.

The process of the invention is preferably carried out with an amount of phenol in excess of stoicheometric quantities; i.e. more than 2 moles of phenol per mole of ketone present in the reaction zone, and preferably between about 3 and about 30 moles of phenol per mole of ketone. A ratio of 6:1 to 20:1 of phenol to ketone is particularly preferred.

The process may be carried out either as a batch or continuous type of operation, although it is preferred to carry out the process continuously. It has been generally established that in such processes, the more intimate the contact between the feedstock and the catalyst, the better the yield of desired product obtained. With this in mind, the present process, when operated as a batch operation, is characterized by the use of vigorous mechanical stirring or shaking of the reactants and catalyst.

When employing a continuous process, the feedstreams may be contacted with the catalyst in any suitable reactor. In one embodiment, the catalyst is packed in a vertical, tubular reactor bed with inert supports, such as ceramic balls or silicon carbide, above and below the catalyst to prevent entrainment of the solid catalyst. In a further embodiment, the catalyst is mixed with an inert material, such as quartz, and loaded in the reactor so as to improve the fluid dynamics of the system. The flow of the reactant feed stream may be upflow or downflow.

Reaction temperature is varied between about 20° and about 150° C depending upon the type of products desired. The reaction temperature must be kept well below about 225° C due to the lack of stability of the catalyst at temperatures of over 250° C. A preferred temperature range is between about 40° and about 100° C. In general, the activity of the catalyst is greater at the higher temperatures.

In general, the pressure in the reaction zone is maintained to keep the reactants in the liquid phase, and accordingly, will vary with the reactants employed and the reaction temperatures. Typical reaction zone pressure varies from about 10 psig to about 2,000 psig.

The weight hourly space velocity effectively measures the catalyst concentration employed, and hence also measures the relative activity of the catalyst. Weight hourly space velocity (WHSV) is defined as the weight per hour of total feed divided by the weight of catalyst employed. The WHSV typically varies between about 0.5 and about 10.0 $hr^{-1}$, preferably about 1.0 and about 4.0 $hr^{-1}$.

The invention is further illustrated by means of the following Illustrative Embodiments which are given for the purpose of illustration only, and the invention is not to be regarded as limited to any of the specific materials or conditions recited therein.

In the Illustrative Embodiments, the reactor employed was a 16-inch long by 9/16-inch diameter stainless steel tube equipped with a liquid feed downflow inlet. The catalyst bed occupied about 5 inches in the center of the reactor; and on either side of the catalyst bed were packed several grams of carborundum chips.

In all cases, the catalyst bed comprised 5 grams of catalyst mixed with 10 grams of quartz. All Illustrative Embodiments were done in the liquid phase and in a downflow manner.

In all Illustrative Embodiments, the perfluorinated polymer catalyst (prior to partial neutralization) was Nafion 501 powder, having about 0.80 milliequivalents of acid per gram. The theorized structure for the Nafion 501 powder is exemplified by the following repeating structure where $n = 1$ or 2 and the ratio of $x$ over $y$ varies from between 2 and about 50:

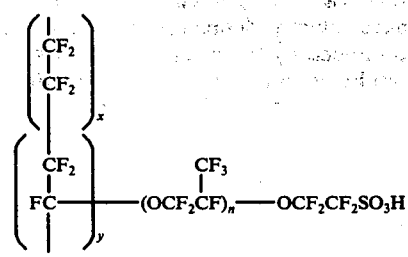

In all Illustrative Embodiments the phenol employed was benzophenol (phenol per se) and the ketone employed was acetone. The selectivity is presented as p,p'-Bisphenol-A[2,2-bis(4-hydroxyphenyl)propane], o,p'-Bisphenol-A[2-(2-hydroxyphenyl)-2-(4-hydroxyphenyl)propane], and codimer [4-(4-hydroxyphenyl)-2,2,4-trimethylchroman].

Illustrative Embodiment I

In Illustrative Embodiment I, the perfluorinated polymer catalyst of structure VII was employed without partial neutralization. The temperature was maintained at 61° C, the phenol to acetone molar ratio at 14.8, and the WHSV at 2.1. The results are presented below in Table 1.

Table 1

| Time, hrs. | 2.5 | 7.5 | 23.5 | 28.5 | 30.5 |
|---|---|---|---|---|---|
| Temperature, ° C | 61 | 61 | 61 | 61 | 61 |
| WHSV | 2.1 | 2.1 | 2.1 | 2.1 | 2.1 |
| Acetone Conversion, %w | 36 | 34 | 34 | 33 | 33 |
| Selectivity, %w | | | | | |
| p,p'-Bisphenol-A | 82 | 82 | 83 | 83 | 83 |
| o,p'-Bisphenol-A | 14.5 | 14.5 | 14 | 14 | 14 |
| Codimer | 3.5 | 3.5 | 3 | 3 | 3 |

Illustrative Embodiment II

Illustrative Embodiments II through V disclose the use of a catalyst of the structure VII (employed in Illustrative Embodiment I) partially neutralized with 2-mercaptoethylamine (also called 2-aminoethanethiol). The catalyst for Illustrative Embodiment II was prepared by dissolving 0.157 grams (1.38 m. moles) of 2-aminoethanethiol hydrochloride in 100 milliliters (ml) of water and then adding 5.8 grams of 150 micrometer particle size Nafion 501 powder. The mixture was stirred for 3 hours, and the solid was collected by filtration and washed with fifteen 10 ml portions of water. The catalyst was then dried in a vacuum oven at 80° C and 3 mm pressure for 16 hours. Titration revealed that the catalyst product contained 0.56 m equiv. of acid, or in the other words, that 30% of the acid sites were neutralized.

This partially neutralized catalyst was employed at a phenol to acetone molar ratio of 14.8 and at varying temperatures and WHSV. The results are presented below in Table 2.

Table 2

| Time, hrs. | 3.5 | 22 | 23 | 25 | 29 | 46 | 52 |
|---|---|---|---|---|---|---|---|
| Temperature, ° C | 61 | 61 | 61 | 61 | 61 | 55 | 55 |
| WHSV | 2.1 | 2.1 | 2.1 | 4.2 | 4.2 | 2.1 | 2.1 |
| Acetone Conversion, %w | 88 | 89.5 | 89.5 | 82 | 80 | 81 | 82 |
| Selectivity, %w | | | | | | | |
| p,p'-Bisphenol-A | 97.5 | 97.5 | 97.5 | 97.5 | 97.5 | 98.0 | 98.0 |
| p,p'-Bisphenol-A | 2.5 | 2.5 | 2.5 | 2.5 | 2.5 | 2.0 | 2.0 |

Illustrative Embodiment III

The catalyst of Illustrative Embodiment III differs from the catalyst of Illustrative Embodiment II in that the amount of 2-aminoethanethiol hydrochloride added was sufficient to neutralize only 20% of the acid groups. WHSV was maintained at 2.1 and temperature at 61° C. The phenol to acetone ratio was increased from 11.8 to 14.8 after about 16 hours. The results are presented below in Table 3.

Table 3

| Time, hrs. | 2 | 7 | 14.5 | 22 | 24 | 42.5 | 48 |
|---|---|---|---|---|---|---|---|
| Temperature, ° C | 61 | 61 | 61 | 61 | 61 | 61 | 61 |
| Phenol/Acetone Molar Ratio | 11.8 | 11.8 | 11.8 | 14.8 | 14.8 | 14.8 | 14.8 |
| Acetone Conversion, %w | 80 | 80 | 78 | 78 | 82 | 86 | 87 |
| Selectivity, %w | | | | | | | |
| p,p'-Bisphenol-A | 97.0 | 97.0 | 97.2 | 97.0 | 97.0 | 97.0 | 97.0 |

Table 3-continued

| | | | | | | | |
|---|---|---|---|---|---|---|---|
| o,p'-Bisphenol-A | 3.0 | 3.0 | 2.8 | 3.0 | 3.0 | 3.0 | 3.0 |

Illustrative Embodiment IV

Illustrative Embodiment IV was conducted in a similiar manner to Illustrative Embodiment II and III except that the catalyst was 10% neutralized. WHSV was 2.1, phenol to acetone ratio was 14.8 and the reaction temperature was 61° C. The results are presented below in Table 4.

Table 4

| Time, hrs. | 5.5 | 25 | 31 | 46.5 | 49.5 | 52.5 |
|---|---|---|---|---|---|---|
| Temperature, ° C | 61 | 61 | 61 | 61 | 61 | 61 |
| Acetone Conversion, %w | 80 | 80 | 80 | 80 | 79 | 79 |
| Selectivity, %w | | | | | | |
| p,p'-Bisphenol-A | 95.5 | 95.3 | 95.0 | 95.2 | 95.0 | — |
| o,p'-Bisphenol-A | 4.5 | 4.7 | 5.0 | 4.8 | 5.0 | — |

Illustrative Embodiment V

Illustrative Embodiment V was conducted similiar to Illustrative Embodiment IV except that the catalyst was 45% neutralized. WHSV was kept at 2.1, the phenol to acetone molar ratio at 14.8, and the reaction temperature at 61° C. The results are presented below in Table 5.

Table 5

| Time, hrs. | 4 | 5.5 | 23 | 28 | 47 | 49 |
|---|---|---|---|---|---|---|
| Temperature, ° C | 61 | 61 | 61 | 61 | 61 | 61 |
| Acetone Conversion, %w | 86 | 86.5 | 86 | 85 | 83 | 83 |
| Selectivity, %w | | | | | | |
| p,p'-Bisphenol-A | 97.5 | 97.5 | 97.8 | 97.5 | 97.3 | 97.3 |
| o,p'-Bisphenol-A | 2.5 | 2.5 | 2.2 | 2.5 | 2.7 | 2.7 |

What is claimed is:

1. A process for the production of bisphenols which comprises contacting a phenol and ketone in the liquid phase at a temperature of between about 20° and about 150° C with a solid perfluorinated polymer catalyst having pendent sulfonic acid groups modified by the neutralization of between about 5 and about 50 percent of the sulfonic acid groups with a $C_1$-$C_4$ alkyl mercaptoamine wherein said solid perfluorinated polymer catalyst prior to partial neutralization contains a repeating structure selected from the group consisting of:

a)
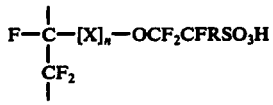

or b)
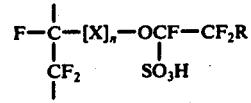

where n is 0, 1 or 2; R is a radical selected from the group consisting of fluorine and perfluoroalkyl radicals having from 1 to 10 carbon atoms; and X is selected from the group consisting of:

[O(CF$_2$)$_m$] , [OCF$_2$CFY] or [OCFYCF$_2$[ where m is an integer from 2 to 10 and Y is a radical selected from the class consisting of fluorine and the trifluoromethyl radical.

2. A process according to claim 1 wherein said perfluorinated catalyst contains the repeating structure:

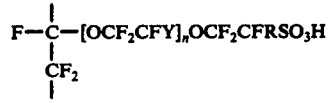

3. A process according to claim 1 wherein said perfluorinated catalyst contains the repeating structure:

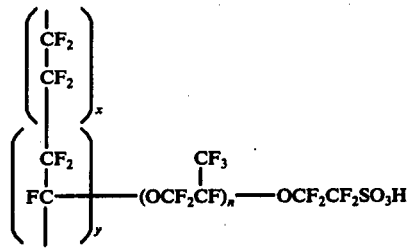

4. A process according to claim 1 wherein said phenol is phenol per se, said ketone is acetone, and said bisphenol is 2,2-bis(4-hydroxyphenyl)propane.

5. A process according to claim 4 wherein the molar ratio of phenol per se to acetone is between about 6:1 and about 20:1.

6. A process according to claim 1 wherein said alkyl mercaptoamine is 2-mercaptoethylamine.

7. A process according to claim 1 wherein the weight hourly space velocity, defined as the weight per hour of total feed divided by the weight of catalyst employed, varies from between about 0.5 and about 10.0 hr$^{-1}$.

* * * * *